(12) United States Patent
Iversen et al.

(10) Patent No.: US 8,888,864 B2
(45) Date of Patent: Nov. 18, 2014

(54) ENERGY STORING FOOT PLATE

(75) Inventors: Edwin Kay Iversen, Salt Lake City, UT (US); Harold H. Sears, Salt Lake City, UT (US); Arthur D. Dyck, Draper, UT (US); Steven R. Kunz, Salt Lake City, UT (US); Joseph Anthony Jacobs, Salt Lake City, UT (US); James R. Linder, West Jordan, UT (US); Melinda Linder, legal representative, West Jordan, UT (US); Peter K. Strazdins, Park City, UT (US)

(73) Assignee: Motion Control, Salt Lake City, UT (US)

( * ) Notice: Subject to any disclaimer, the term of this patent is extended or adjusted under 35 U.S.C. 154(b) by 901 days.

(21) Appl. No.: 12/470,365

(22) Filed: May 21, 2009

(65) Prior Publication Data

US 2009/0319055 A1 Dec. 24, 2009

Related U.S. Application Data

(63) Continuation-in-part of application No. 11/394,331, filed on Mar. 29, 2006.

(60) Provisional application No. 60/666,388, filed on Mar. 29, 2005.

(51) Int. Cl.
| | |
|---|---|
| *A61F 2/66* | (2006.01) |
| *A61F 2/68* | (2006.01) |
| *A61F 2/72* | (2006.01) |
| *A61F 2/30* | (2006.01) |
| *A61F 2/50* | (2006.01) |
| *A61F 2/70* | (2006.01) |
| *A61F 2/74* | (2006.01) |
| *A61F 2/76* | (2006.01) |

(52) U.S. Cl.
CPC ............... *A61F 2/68* (2013.01); *A61F 2/6607* (2013.01); *A61F 2/72* (2013.01); *A61F 2002/30359* (2013.01); *A61F 2002/5003* (2013.01); *A61F 2002/5006* (2013.01); *A61F 2002/5033* (2013.01); *A61F 2002/6614* (2013.01); *A61F 2002/6685* (2013.01); *A61F 2002/6854* (2013.01); *A61F 2002/704* (2013.01); *A61F 2002/741* (2013.01); *A61F 2002/744* (2013.01); *A61F 2002/745* (2013.01); *A61F 2002/748* (2013.01); *A61F 2002/7625* (2013.01); *A61F 2220/0033* (2013.01)
USPC ............................................................ 623/48

(58) Field of Classification Search
CPC ............................... A61F 2/6607; A61F 2/66
USPC ............................................................ 623/48
See application file for complete search history.

(56) References Cited

U.S. PATENT DOCUMENTS

| | | |
|---|---|---|
| 1,051,288 A | 1/1913 | Szydlowski |
| 3,820,168 A | 6/1974 | Horvath |

(Continued)

FOREIGN PATENT DOCUMENTS

WO     WO 9304645 A1 *  3/1993

*Primary Examiner* — Bruce E Snow
*Assistant Examiner* — Melissa Hoban
(74) *Attorney, Agent, or Firm* — Thorpe North & Western LLP

(57) ABSTRACT

Compositions are provided for a prosthetic ankle comprising: a joint housing having a bottom surface, a clevis coupled to the joint housing such that the clevis can rotate about the joint housing, a prosthetic coupling structure that couples the clevis to an amputee, and an articulating joint contained in the joint housing. Additionally, a portion of the bottom surface of the joint housing can be curved allowing a substrate a preset amount of flexion when coupled thereto and flexed in a concave position.

19 Claims, 3 Drawing Sheets

(56) References Cited

U.S. PATENT DOCUMENTS

| | | |
|---|---|---|
| 3,883,900 A | 5/1975 | Jerard et al. |
| 4,442,554 A * | 4/1984 | Copes .............................. 623/52 |
| 4,721,510 A * | 1/1988 | Cooper et al. .................. 623/55 |
| 5,704,945 A | 1/1998 | Wagner et al. |
| 5,957,981 A | 9/1999 | Gramnas |
| 6,106,560 A | 8/2000 | Boender |
| 6,187,052 B1 | 2/2001 | Molino et al. |
| 6,443,993 B1 | 9/2002 | Koniuk |
| 6,719,807 B2 * | 4/2004 | Harris .............................. 623/55 |
| 6,764,521 B2 | 7/2004 | Molino et al. |
| 7,347,877 B2 | 3/2008 | Clausen et al. |
| 2005/0137717 A1 | 6/2005 | Gramnas et al. |
| 2006/0235544 A1 | 10/2006 | Iversen |

\* cited by examiner

ENERGY STORING FOOT PLATE

CROSS-REFERENCE TO RELATED APPLICATIONS AND CLAIM OF PRIORITY

This is a continuation-in-part of U.S. patent application Ser. No. 11/394,331 filed on Mar. 29, 2006, which is a nonprovisional of U.S. provisional patent application Ser. No. 60/666,388, filed on Mar. 29, 2005, which are hereby incorporated by reference in their entirety.

FIELD OF THE INVENTION

The present invention relates generally to prosthetic devices.

BACKGROUND

An intact human foot, connected to its ankle, travels through stance and swing phases of a gait cycle during each stride of motion, whether the motion involves walking, jogging, or running. By adjusting the stiffness and damping characteristics of a prosthetic ankle or foot mechanism, the springiness of the intact natural human foot and its corresponding natural human joints may be mimicked, thereby optimizing the prosthetic for the desired motion of the wearer. The characteristics that are desired to store and release energy appropriately for walking tend to oppose those best suited to fast walking and running.

In a stance phase, the foot is in contact with the ground and the weight of a person is supported on the foot. In a swing phase, the foot is off the ground as the entire leg and foot move from a posterior position to an anterior position with respect to a center of gravity of the person.

The stance phase A, as shown in FIG. 1, begins just after completion of the swing phase and commences with a heel strike wherein the foot is lowered to the ground as the body moves forward from a position posterior to the person's center of gravity. Immediately after heel strike, the foot moves from a dorsi-flexed position, wherein the toes of the foot are pointed upwards, to a plantar-flexed position B wherein the bottom of the foot or shoe is flat on the walking surface, which provides greater stability as the entire weight of the person is shifted over the foot in contact with the ground.

The swing phase C commences just after heel strike of the other foot. During the swing phase, the foot is again in the dorsi-flexed position D as the foot leaves the walking surface and the foot and leg swing forward in preparation for the stance phase. Dorsi-flexion is important for normal human locomotion, since the toes are dorsi-flexed in order to clear the floor. If the foot is not dorsi-flexed during the swing phase, it would most likely catch on the walking surface and cause the person to stumble and fall, which may lead to serious injury.

It is beneficial for the joint mechanism of a prosthetic ankle or foot to have the ability to resist plantar flexion at heel strike and to store energy during dorsi flexion/extension. During the swing phase, lifting the toe is also desirable. If the dynamic response is too stiff, the foot bounces back too quickly. If the spring is too soft, it stores less energy and releases too late.

SUMMARY OF THE INVENTION

In accordance with one embodiment of the present invention, a prosthetic ankle can comprise: a joint housing having a bottom surface, a clevis coupled to the joint housing such that the clevis can rotate about the joint housing, a prosthetic coupling structure that couples the clevis to an amputee, and an articulating joint contained in the joint housing. Additionally, a portion of the bottom surface of the joint housing can be curved allowing a substrate a preset amount of flexion when coupled thereto and flexed in a concave position.

In one embodiment, a prosthetic foot can comprise: a sole plate, a joint housing having a bottom surface, a clevis coupled to the sole plate and the joint housing such that the clevis can rotate about the joint housing, and a prosthetic coupling structure that couples the clevis to an amputee. Additionally, as discussed above, a portion of the bottom surface of the joint housing can be curved allowing a substrate a preset amount of flexion when coupled thereto and flexed in a concave position.

In another embodiment, a prosthetic foot can comprise: a sole plate, a joint housing having a bottom surface, a clevis coupled to the sole plate and the joint housing such that the clevis can rotate about the joint housing, a toe-off spring coupled to at least a portion of the sole plate, a toe-lift spring coupled to at least a portion of the toe-off spring and the clevis, and a rotary hub disposed within the joint housing and configured to act as an articulating joint. Additionally, as discussed above, a portion of the bottom surface of the joint housing can be curved allowing a substrate a preset amount of flexion when coupled thereto and flexed in a concave position.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
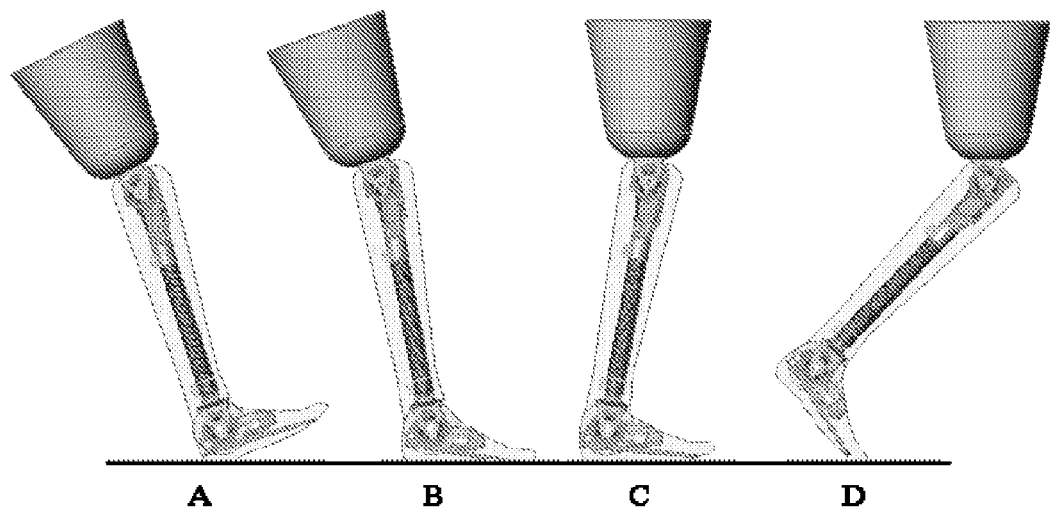
FIG. 1 is an illustration showing the stance phase features of a knee/ankle prosthetic system.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the context clearly dictates otherwise.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a substrate that is "substantially free of" flexion would either completely lack flexion, or so nearly completely lack flexion that the effect would be the same as if it completely lacked flexion. In other words, a composition that is "substantially free of" a characteristic or element may still contain such a characteristic or element as long as there is no measurable effect thereof.

As used herein, "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

It has been recognized that it would be advantageous to develop a prosthetic ankle allowing for improved flexion for amputees. Specifically, the present inventors have recognized the need for a prosthetic ankle having a curved joint housing allowing for a preset amount of flexion for a substrate coupled thereto. In accordance with this, embodiments for a prosthetic ankle and foot are provided herein. When discussing embodiments and structures herein, the present specification can refer to a prosthetic ankle or a prosthetic foot, and each of these discussions can be considered applicable to each of these embodiments, whether or not they are explicitly discussed in the context of that embodiment. For example, in discussing a joint housing for a prosthetic ankle, such a joint housing can also be used in a prosthetic foot, and vice versa.

Figure 2:
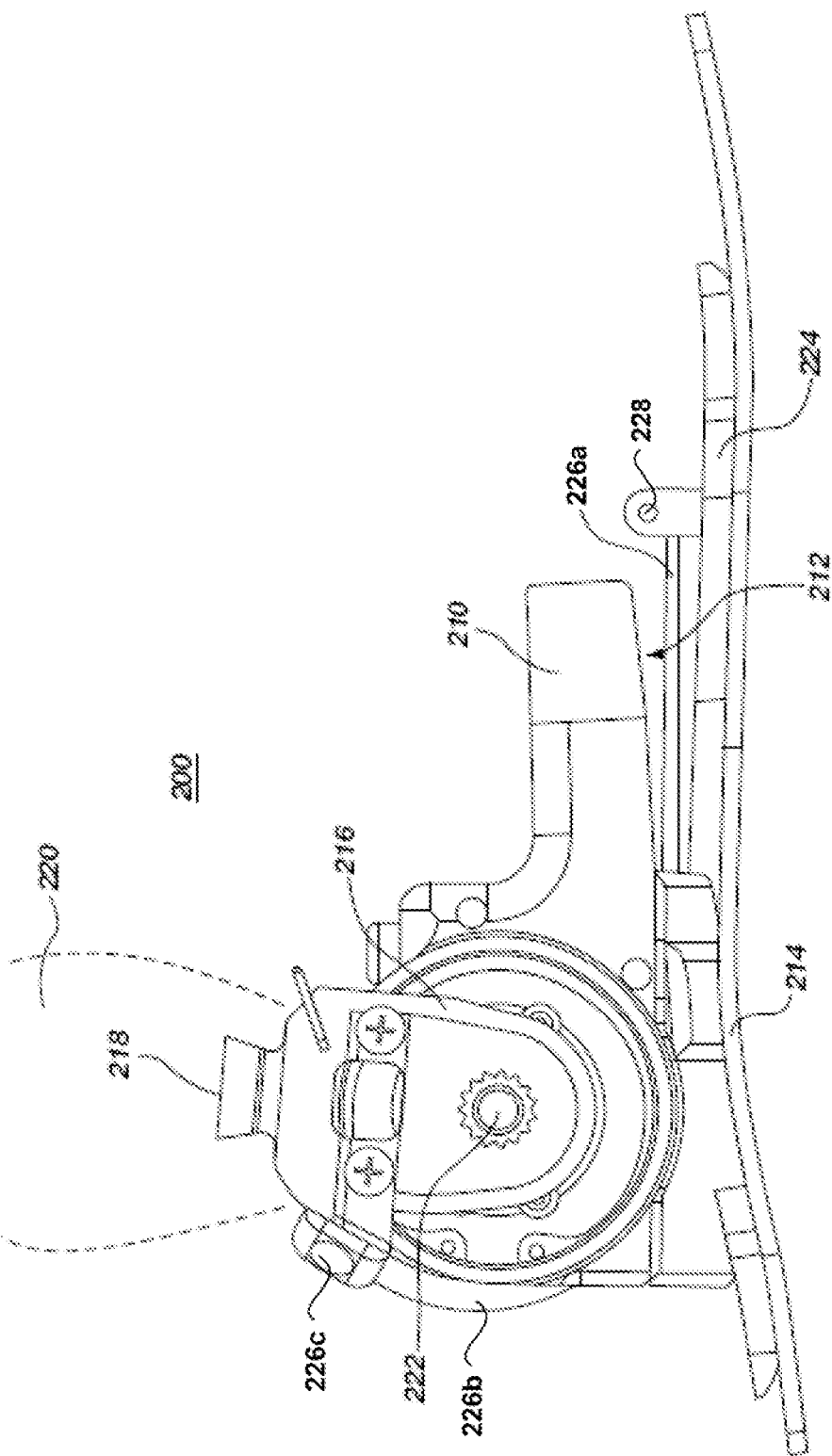
FIG. 2 is a side view of a prosthetic foot having a prosthetic ankle in accordance with an embodiment of the present invention.

As illustrated in FIG. 2, the prosthetic foot 200 can have a joint housing 210 with a bottom curved surface 212 to allow a preset amount of flexion of the substrate when coupled thereto and flexed in a concave position. A clevis 216 can be coupled to the joint housing such that the clevis can rotate about the joint housing. A prosthetic coupling structure 218 can couple the clevis to an amputee 220. Additionally, an articulating joint (e.g., rotary hub 222) can be coupled to the joint housing.

As discussed above, the present elements are equally applicable to a prosthetic ankle which can comprise a joint housing 210 with a bottom surface curved 212 to allow a preset amount of flexion of a substrate when coupled thereto and flexed in a concave position; a clevis 216 coupled to the joint housing such that the clevis can rotate about the joint housing; and a prosthetic coupling structure 218 that couples the clevis to an amputee 220. As such, a prosthetic ankle comprises, at a minimum, a joint housing, a clevis, and a prosthetic coupling structure while a prosthetic foot comprises, at a minimum, a prosthetic ankle coupled to a substrate.

In one embodiment, the substrate can be a sole plate 214 such that the prosthetic foot comprises a sole plate, a joint housing having a bottom surface, a clevis coupled to the sole plate and the joint housing such that the clevis can rotate about the joint housing, and a prosthetic coupling structure that couples the clevis to an amputee. Additionally, the substrate can be selected from the group consisting of a sole plate, a toe-off spring, a toe-lift spring, or combinations thereof.

In another embodiment, the prosthetic foot can further comprise a toe-off spring 224 coupled to at least a portion of the sole plate and a toe-lift spring 226a, 226b, 226c coupled to at least a portion of the toe-off spring and the clevis. A first end 226c of the toe-lift spring can be coupled to the clevis 216 and a second end 226a of the toe-lift spring can move between the joint housing 210 and the toe-off spring. A toe-lift spring retainer 228 coupled the toe-off spring can restrict movement of the second end of the toe-lift spring in an direction perpendicular to a plane of the toe-off spring. Additionally, a portion of the bottom surface of the joint housing can be curved allowing the toe-off spring and the toe-lift spring a preset amount of flexion when flexed in a concave position.

Additionally, the prosthetic foot can comprise a toe-off spring coupled to at least a portion of the sole plate and the clevis. Additionally, a portion of the bottom surface of the joint housing can be curved allowing the flexed substrate to transfer a preset amount of flexion to the toe-off spring when flexed in a concave position.

In one embodiment, the prosthetic foot can further comprise a toe-lift spring coupled to at least a portion of the sole plate and the clevis. Additionally, a portion of the bottom surface of the joint housing can be curved allowing the flexed substrate to transfer a preset amount of flexion to the toe-lift spring when flexed in a concave position.

The articulating joint described herein can be selected from the group consisting of rotary hub, ball and socket, hinge and pin, roller bearing, and ball bearing. The prosthetic ankle or foot can further comprise a locking mechanism that locks the articulating joint with respect to the joint housing. As such, the locking mechanism can be a ratchet and pawl mechanism. Such a ratchet and pawl mechanism need only have a minimum of one locking position although several locking positions are also possible and contemplated herein.

In one embodiment, the joint housing can be coupled to the substrate though the clevis. In addition, the joint housing can be semi-rigidly coupled to the sole plate. In another aspect, the clevis can be coupled to the substrate, e.g. sole plate, in at least two locations. In another aspect, the clevis can be semi-rigidly coupled to the toe-off spring. In another aspect, the joint housing can be semi-rigidly coupled to the toe-off spring. In another aspect, the toe-lift spring can be semi-rigidly coupled to the toe-off spring.

Figure 3:
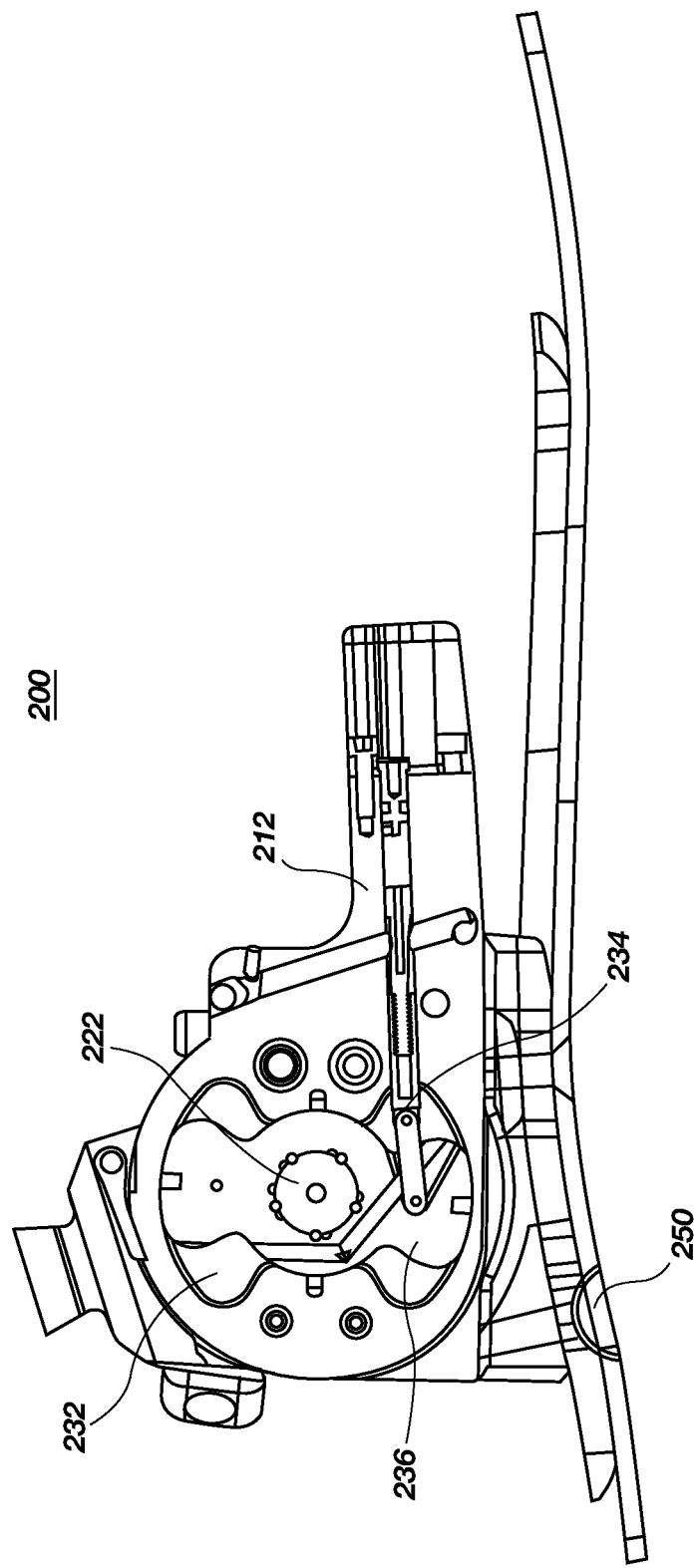
FIG. 3 is a cross-sectional side view of a prosthetic foot having a prosthetic ankle in accordance with an embodiment of the present invention.

Turning now to FIG. 3, the prosthetic foot 200, including the prosthetic ankles described herein, can have an articulating joint, e.g., rotary hub 222, and a joint housing 212 forming a first chamber 232 having a first opening 234 such that the prosthetic foot further comprises a vane 236 extending outwardly from the rotary hub, wherein the vane is configured to actuate fluid flow through the first opening.

Specifically, the first chamber can have a first opening that allows hydraulic fluid to pass through it. The rotary hub may be a rotating shaft bearing. The bearings may be high load needle bearings that are convoluted internal to the rotary hub to minimize width and provide an extremely strong ankle bearing. Alternatively, the ankle may rotate around this hub axis or rotary axle using some other type of bearings (e.g., ball bearings). In one embodiment, a rotary actuator is the combination of the joint housing, rotary hub and vane(s). By placing the bearings internal to the rotary hub, the moments on the vanes are reduced and this allows lighter construction materials to be used for the bearing.

A vane can extend outwardly from the rotary hub. The vane is configured to actuate fluid flow through the first opening. This provides hydraulic resistance to the substrate and joint body or housing. The first opening can lead to a fluid passageway that has flow elements, venturi structures, and/or valves stationed along the passage which restrict fluid flow under certain conditions or cause it to be diverted to other sub-branches of the passageway.

In addition, check valves can be coupled to the fluid flow in the fluid passageway or sub-passage way to allow the passage of fluid in one direction but not in the other. The fluid passageway can allow fluid to flow in a certain direction corresponding to rotary hub motion subtending plantar-flexion motion of the prosthetic joint, and conversely, allow fluid to flow in the opposing direction corresponding to rotary hub motion subtending dorsi-flexion motion of the prosthetic joint. This allows the length of path traveled by the fluid when it flows in one direction to be equal to that traveled when the fluid flows in the opposite direction.

The present inventors have recognized that the employment of a rotary action vane-type actuator at each joint has important advantages over use of one or more linear piston-type actuators to serve each joint, like those primarily observed in prior art. Rotary actuation accommodates a range of flexion angulation (at least 104 degrees) which exceeds what is achievable with a linear actuator when combined with its necessary linkages, particularly in the very limited space that is available in a prosthetic application.

The nature of the vane action rotating in a chamber of circular cross-sectional profile (when viewed from the side) equalizes the supply versus return fluid path lengths, which tends to balance the internal fluid viscous/friction forces, and thereby directly allows the load to be balanced. This is also a significant advantage in terms of minimizing effort the amputee must input to overcome overhead created by design element motion.

The prosthetic foot or ankle can have an ankle joint with a sufficiently small size to enable it to fit within typical shoe sizes. The reduced size can be accomplished by the rotary hydraulic actuator allowing a vane-like element having pressure surfaces of a sufficiently generous area to keep working fluid pressures below unfeasible threshold values.

The substrate may be coupled to the bottom side of the joint housing with a single pivot point coupling 250, to enable a restricted rotation of the substrate about the device axis. Alternatively, the substrate may be mounted on a spherical or cylindrical surface in order to rotate and facilitate resistance to eversion or inversion. When the substrate is coupled to the joint housing, this allows the substrate to store and release energy during the third rocker portion of the stance gait cycle.

Although intended to mimic the natural anatomy, field testing has demonstrated that more lateral roll can contribute to an amputee's stumbling due to the user stepping on a ground protruding obstacle. Mitigating the initial restore-to-center-upright moment action is valuable, and this permits a relatively relaxed hinge or spherical joint connection to be used where resistance to deflection becomes significant, and the deflection is felt by the user only once this deflection grows to a significant angular deviation from neutral. Thus, a user, who feels an obstacle underfoot, does not experience an upper torso de-stabilizing moment, which is the reaction to the moment induced when a strong restore-to-centre-upright moment is initiated between the body of the ankle joint (foot) and its base-plate (keel). The use of a spherical or cylindrical surface reduces the tendency for stumbling on the limb, which is undergoing the course of stance phase contact.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

The invention claimed is:

1. A prosthetic ankle, comprising:
a substrate;
a joint housing having a bottom surface;
a clevis coupled to the joint housing such that the clevis can rotate about the joint housing;
a prosthetic coupling structure for coupling the clevis to an amputee;
an articulating joint contained in the joint housing;
wherein a portion of the bottom surface of the joint housing is curved allowing the substrate a preset amount of flexion when coupled thereto and flexed in a concave position;
a toe-off spring coupled to at least a portion of the substrate;
a toe-lift spring coupled to at least a portion of the clevis, wherein at least a portion of the toe-lift spring is between the joint housing and the toe-off spring; and
wherein a portion of the bottom surface of the joint housing is curved allowing the toe-off spring and the toe-lift spring a preset amount of flexion when flexed in a concave position.

2. The prosthetic ankle of claim 1, wherein the articulating joint is selected from the group consisting of rotary hub, ball and socket, hinge and pin, roller bearing, and ball bearing.

3. The prosthetic ankle of claim 2, wherein the articulating joint is a rotary hub and the joint housing forms a first chamber having a first opening and wherein the prosthetic ankle further comprises a vane extending outwardly from the rotary hub, wherein the vane is configured to actuate fluid flow through the first opening.

4. The prosthetic ankle of claim 1, further comprising a locking mechanism that locks the articulating joint with respect to the joint housing.

5. The prosthetic ankle of claim 4, wherein the locking mechanism is a ratchet and pawl mechanism.

6. The prosthetic ankle of claim 1, wherein the clevis is coupled to the substrate through the joint housing.

7. The prosthetic foot of claim 1, wherein the substrate is concave on the surface furthest from the joint housing.

8. A prosthetic foot, comprising:
a sole plate;
a joint housing having a bottom surface;
a clevis coupled to the sole plate and the joint housing such that the clevis can rotate about the joint housing;
a prosthetic coupling structure for coupling the clevis to an amputee;
wherein a portion of the bottom surface of the joint housing is curved allowing the sole plate a preset amount of flexion when flexed in a concave position;
a toe-off spring coupled to at least a portion of the sole plate, and wherein the joint housing is semi-rigidly coupled to the toe-off spring;
a toe-lift spring coupled to at least a portion of the toe-off spring and the joint housing;

a toe-lift spring retainer coupled to the toe-off spring to restrict movement of an end of the toe-lift spring in a direction perpendicular to a plane of the toe-off spring; and wherein a portion of the bottom surface of the joint housing is curved allowing the toe-off spring and the toe-lift spring a preset amount of flexion when flexed in a concave position.

9. The prosthetic foot of claim 8, wherein the clevis is coupled to the joint housing in at least two locations.

10. The prosthetic foot of claim 8, wherein the joint housing is semi-rigidly coupled to the toe-off spring.

11. The prosthetic foot of claim 8, wherein the joint housing is semi-rigidly coupled to the sole plate.

12. The prosthetic foot of claim 8, further comprising an articulating joint contained in the joint housing.

13. The prosthetic foot of claim 12, wherein the articulating joint is selected from the group consisting of a rotary hub, a ball and socket, a hinge and pin, a roller bearing, and a ball bearing.

14. The prosthetic foot of claim 13, wherein the articulating joint is a rotary hub and the joint housing forms a first chamber having a first opening and wherein the prosthetic ankle further comprises a vane extending outwardly from the rotary hub, wherein the vane is configured to actuate fluid flow through the first opening.

15. The prosthetic foot of claim 12, further comprising a locking mechanism that locks the articulating joint with respect to the joint housing.

16. The prosthetic foot of claim 15, wherein the locking mechanism is a ratchet and pawl mechanism.

17. The prosthetic foot of claim 8, wherein the sole plate is concave on the surface furthest from the joint housing.

18. A prosthetic foot, comprising:
a sole plate;
a joint housing having a bottom surface;
a clevis coupled to the sole plate and the joint housing such that the clevis can rotate about the joint housing;
a toe-off spring coupled to at least a portion of the sole plate;
a toe-lift spring coupled to at least a portion of the clevis, wherein at least a portion of the toe-lift spring is between the joint housing and the toe-off spring; and
a rotary hub disposed within the joint housing and configured to act as an articulating joint;
wherein a portion of the bottom surface of the joint housing is curved allowing the toe-off spring and the toe-lift spring a preset amount of flexion when flexed in a concave position.

19. The prosthetic foot of claim 18, wherein the toe-lift spring is semi-rigidly coupled to the toe-off spring.

* * * * *